United States Patent [19]

Lynnworth

[11] Patent Number: 4,735,097
[45] Date of Patent: Apr. 5, 1988

[54] METHOD AND APPARATUS FOR MEASURING FLUID CHARACTERISTICS USING SURFACE GENERATED VOLUMETRIC INTERROGATION SIGNALS

[75] Inventor: Lawrence C. Lynnworth, Waltham, Mass.

[73] Assignee: Panametrics, Inc., Waltham, Mass.

[21] Appl. No.: 765,003

[22] Filed: Aug. 12, 1985

[51] Int. Cl.$^4$ .................. G01F 1/66; G01F 1/712; G01F 23/28
[52] U.S. Cl. .................. 73/861.28; 73/290 V; 73/861.06; 73/53
[58] Field of Search .......... 73/861.06, 861.18, 861.27, 73/861.28, 597, 290 V, 32 A, 53; 310/313 R

[56] References Cited

U.S. PATENT DOCUMENTS

| | | |
|---|---|---|
| 2,787,160 | 4/1957 | Van Valkenburg . |
| 3,512,400 | 5/1970 | Lynnworth . |
| 3,911,726 | 10/1975 | Georgiev .......... 73/597 X |
| 3,987,674 | 10/1976 | Baumoel . |
| 4,098,117 | 7/1978 | Baumoel . |
| 4,103,551 | 8/1978 | Lynnworth . |
| 4,118,983 | 10/1978 | Brazhnikov .......... 73/290 V |
| 4,232,548 | 11/1980 | Baumoel . |
| 4,286,470 | 9/1981 | Lynnworth . |
| 4,320,659 | 3/1982 | Lynnworth et al. . |
| 4,333,353 | 6/1982 | Baumoel . |
| 4,336,719 | 6/1982 | Lynnworth . |
| 4,373,401 | 2/1983 | Baumoel . |
| 4,375,767 | 3/1983 | Magori .......... 73/861.18 |
| 4,425,803 | 1/1984 | Baumoel . |
| 4,467,659 | 8/1984 | Baumoel . |
| 4,475,054 | 10/1984 | Baumoel . |

FOREIGN PATENT DOCUMENTS 304502 3/1972 U.S.S.R. .......... 73/861.28

OTHER PUBLICATIONS

K. Toda et al., "A Technique for Measuring the Sound Velocity . . . Two Liquids", J. Acoust. Soc. Am., vol. 68, No. 4, 10/1980, pp. 1053-1055.

Mason et al, *Physical Acoustics*, vol. XIV, Academic Press, 1979, pp. 431, 475.
Permag Alnico 5 Catalog No. CU-511.
Lynnworth, "(no title given)", *Trans. Institute of Measurement and Control*, vol. 4, No. 1, p. 6, Jan.-Mar., 1982.
Lynnworth, "Liquid Level Measurements Using Longitudinal, Shear, External and Torsional Waves", *Proc. IEEE Ultrasonics Symposium*, 1979, pp. 186-194, 6/84.
Baumoel, "Clamp-On Transit Time Ultrasonic Flowmeters", *Measurement and Control*, pp. 186-194, Jun., 1984.
Brower et al., IEEE Trans., *Sonics and Ultrasonics*, SU-26(4) 306-308, Jul., 1979.
McMaster, *NDT Handbook*, Sect. 43, pp. 8. 10-11, Ronald Press, NY (1959).

(List continued on next page.)

*Primary Examiner*—Charles A. Ruehl
*Attorney, Agent, or Firm*—Lahive & Cockfield

[57] ABSTRACT

A method and apparatus for measuring fluid characteristics use a non-invasive ultrasonic system for generating spatially extended signals into a volume of a fluid and detecting said signals for measuring the characteristic of the fluid. The generated waves are Rayleigh-like surface waves creating, in effect, an extended aperture transducer from which the waves leak into the fluid. The Rayleigh-like surface wave operates in an environment wherein the plate or other structure on which the surface wave is generated has a thickness, normal to the primary direction of propagation of the wave, of less than four Rayleigh wavelengths and greater than approximately one-half of a Rayleigh wavelength. The extended aperture has a length of at least about ten Rayleigh wavelengths. The excitation for the system is generally a short pulse interrogation in order to avoid those interferences which may cause Lamb waves to be set up in the solid material. Several different configurations employing the Rayleigh-like surface wave are illustrated and discussed.

40 Claims, 4 Drawing Sheets

OTHER PUBLICATIONS

*Conference & Exhibition Guide*, Ultrasonics International 85, Jul. 2–4, 1985, London.

Krautkramer et al., *Ultrasonic Testing of Materials*, 3rd Ed., Springer-Verlag, Berlin, Heidelberg, New York, 1983, pp. 44–45, 608–609, 618.

Bertoni et al., "Unified Theory of Rayleigh-Angle Phenomena for Acoustic Beams at Liquid-Solid Interfaces", *Applied Physics*, 2.157, 164, 172 (1973), Springer-Verlag.

"Model 6001 Ultrasonic Flowmeter", Copyright 1984, Panametrics, Inc., Waltham, Mass.

*IEEE Transactions on Biomedical Engineering*, vol. BME-32, No. 7, Jul., 1985, pp. 530–531, 535.

Frederick, *Ultrasonic Engineering*, John Wiley & Sons, New York, 1965.

Thoi et al, "On the Averaging Technique and the Discharge Coefficient of the Annular-Averaging Flow Sensor", ISA Transactions, vol. 18, No. 1, 1979, pp. 41–42.

Pollard, *Sound Waves in Solids*, Pion Limited, London, 1979, pp. 69–73.

Lynnworth, "Ultrasonic Flowmeters", *Trans. Institute of Measurement and Control*, vol. 3, No. 4, Oct.–Dec. 1981, pp. 217–222, pp. 2–24.

"Clampitron Flowmeter", Controlotron Corporation, Hauppauge, L.I., N.Y., Bulletin 240-2F.

"System 480 Wide Beam Clamp-On Ultrasonic Flowmeter", Controlotron Corporation, Hauppauge, L.I., N.Y., Bulletin 480DS1A.

Arapov et al., "Propagation of Leaky Surface Acoustic Waves in Layered Systems", *Soviet Phys. Acoust.*, 31(2), Mar.–Apr., 1985, pp. 85–87.

METHOD AND APPARATUS FOR MEASURING FLUID CHARACTERISTICS USING SURFACE GENERATED VOLUMETRIC INTERROGATION SIGNALS

BACKGROUND OF THE INVENTION

The invention relates generally to methods and apparatus for measuring fluid characteristics and in particular, to ultrasonic measurement methods and apparatus typically employed for measuring fluid flow characteristics.

Non-invasive, clamp-on transit time doppler or correlation ultrasonic flowmeters have been employed to measure or interrogate fluids, and in particular liquids. The clamp-on flowmeter typically employs longitudinal or shear wave piezoelectric crystals to interrogate the fluid. In many instances the interrogation signals in the fluid are narrow band oblique signals and the flowmeters use transit time measurements to determine the desired characteristics of the fluid being measured.

When it became more desirable to employ a so-called "wide beam" or "broad beam" as the interrogation source, for example a beam extended axially along a conduit such as a pipe or tube, it became customary to employ Lamb waves. Lamb waves in the pipe wall provide an improvement over longitudinal or shear wave interrogation sources in the clamp-on interrogation system because their broad beam axial extent makes it possible to position more easily a pair of communicating transducers. This flexible spacing, unavailable in narrow beam shear wave or longitudinal wave systems, results from a spacing which is relatively independent of the speed of sound in the fluid. Lamb waves, however, have a disadvantage in that they are dispersive. Therefore, when Lamb waves are used, the optimum frequency must be calculated as a function of pipe thickness and composition. Unfortunately, the pipe thickness and composition are not always known precisely at either or both of the transducer locations.

It is also well known that one of the advantages of using a shear wave in the pipe wall over a longitudinal wave is the lower velocity of the shear wave. And further, it is recognized that a surface wave, such as a Rayleigh wave, has a yet lower phase velocity, typically about ten percent lower than a shear wave in a given pipe material. The surface wave is therefore better suited for oblique interrogation of fluids because of the more favorable refraction angles which can be achieved. Unfortunately, however, the Rayleigh wave is also well known to attenuate significantly as the wave "penetrates" into the solid. Thus, if the thickness of a plate, w, is more than one Rayleigh wavelength in thickness (the wavelength corresponding to the wavelength of the Rayleigh wave in the solid), a significant attenuation occurs in the plate. The attenuation increases exponentially as the depth into the solid increases. Accordingly, Rayleigh and Rayleigh-like waves have never been considered practical in connection with clamp-on transducers since the signal which transfers to the fluid has always been thought to be substantially insignificant in strength when compared to the noise in the system. The present invention overcomes the attenuation restriction by means of a synthetic aperture technique.

It is therefore an object of the present invention to provide a fluid measurement apparatus and method employing Rayleigh and Rayleigh-like waves for determining one or more characteristics of the fluid. Other objects of the invention are the designation of the limitations upon the structure of the Rayleigh wave generating apparatus and method in order to effectively measure characteristics of a fluid; the use of Rayleigh-like waves for determining characteristics of a fluid; and the provision of a reliable, sensitive flowmeter detection apparatus and method. Yet further objects of the invention are a low cost, clamp-on ultrasonic transducer system, a liquid level measuring system, and a reliable and inexpensive fluid interrogation system.

SUMMARY OF THE INVENTION

The invention relates generally to an apparatus and method for measuring one or more characteristics of a fluid. The apparatus is used in connection with a plate-like material having a local surface and a remote surface, the remote surface being in contact with the fluid. A transducer is placed in contact with the local surface of the plate-like material; and elements are provided for coupling the transducer to the local surface of the solid material for generating a Rayleigh-like wave having a wavelength $\lambda_R$ in the plate along said local surface. The local surface and the remote surface have a separation, in an interrogation direction, of less than four Rayleigh wavelengths ($4\lambda_R$) and the interrogation direction extends in a direction normal to the local surface.

In another aspect, the method and apparatus for measuring a characteristic of a fluid provide for generating a Rayleigh-like surface wave which is both non-dispersive and which has an intensity at the remote surface substantially less than the intensity at the local surface.

In yet another aspect of the invention, wherein the plate-like material has a thickness greater than one-half of a Rayleigh wavelength, the method and apparatus feature exciting the transducers with a pulse signal sufficiently short to prevent intra-wall interference of the generated energy. In accordance with this aspect of the invention, the Rayleigh-like surface wave is more clearly distinguishable from a Lamb wave which typically has substantially equal energy intensities at both the remote and local surfaces. In particular, the pulse duration should be less than the wall thickness of the plate-like material divided by the velocity of the waves in the solid material.

BRIEF DESCRIPTION OF THE DRAWINGS

Other objects, features, and advantages of the invention will appear from the following description of particular embodiments of the invention taken together with the drawings in which.

DESCRIPTION OF PARTICULAR PREFERRED EMBODIMENTS

The present invention is directed to a surface wave approach for achieving the advantages of a broad beam interrogation, using a synthetic transducer aperture, and yet avoids the shortcomings of a Lamb wave which is a frequency critical dispersive wave having a narrowband spectrum. Furthermore, the illustrated surface wave approach can employ readily available NDT (non-destructive testing) surface wave transducers operating in the frequency decade whose upper limit is at or near one megahertz. This upper frequency is advantageous for oblique interrogation of many liquids flowing in pipes of common wall thickness in the range from about 30 to 300 millimeters in diameter. The actual frequency selected in practice depends largely on the propagation characteristics of the fluid, provided the other constraints underlying this invention are satisfied.

The transducing methods and apparatus described herein thus employ surface waves which closely resemble what would be a Rayleigh wave if the plate into which the surface wave is launched or generated were of substantially infinite thickness. These same transducing methods, however, can also be employed to radiate efficiently through plates that are much thinner than one wavelength. However, the wave, in a plate or membrane of that thickness, is significantly different from a Rayleigh wave in several respects. For example, the source and detection regions are not as extended as they would be for plates having a thickness between about one-half to about four times the Rayleigh wavelength in the plate. By providing a synthetic transducer aperture corresponding to an extended source and detection region, in accordance with the invention and as described in more detail hereinafter, the extended regions, as noted above, allow one to vary substantially the distance between tranducers in the axial direction of the conduit, and thereby be relatively immune to uncertainties or changes in the sound speed $c_3$ in the fluid. Further, one can determine $c_R$ (the velocity of the Rayleigh wave) by applying differential path measurement techniques to the plate, pipe, or other structure being used. The value, $c_R$, can be determined by the slope of the graph of S (the distance between transducers) versus the transit time.

The invention is thus directed to the generation, ideally, of a Rayleigh wave at the surface of a plate or other plate-like structure and the use of that wave in interrogating a fluid. As noted above, however, due to the limited thickness of the plate, a true Rayleigh wave cannot be generated. However, the Rayleigh-like wave which is generated, hereinafter denoted as a "Rayleigh-like surface wave," has several distinguishing characteristics which separate it from similar types of waves such as, for example, a Lamb wave. Thus, the Rayleigh-like surface wave has its energy concentrated near one surface of the plate while falling off exponentially with depth. The Lamb wave, on the other hand, has substantially equal intensity at each boundary of the plate. The phase and group velocities of the Rayleigh-like surface wave are virtually independent of frequency and are equal, that is, the wave is non-dispersive. As will be noted below, the preferred Rayleigh-like surface wave usually is the result of a short, spike-like excitation having a broadband, short pulse characteristic. This prevents possible generation of intra-wall interferences of the energy as is characteristic of, for example, Lamb waves. The pulse duration can be one period or less and should be clearly less than the wall thickness divided by the velocity of the waves in the solid material. This prevents the interferences or build-up of natural resonances which can result in, for example, a Lamb wave. In addition, the Rayleigh wave has no minimum critical spatial width restrictions in order to launch the required wave. This last characteristic enables one to fabricate smaller transducer structures than have been available using Lamb waves.

Other distinctions between the Rayleigh-like surface wave and Lamb-like waves found in a plate, are the general tolerance, subject to the various conditions hereinafter set forth, to deviations in plate thickness, a substantial attenuation of the wave as a function of depth in the plate, and the absence of higher order modes propagating at different velocities.

The mathematical theory for launching Lamb and Rayleigh waves is well known in the art (see for example Krautkrämer, *Ultrasonic Testing of Materials*, 3rd Ed. (1983) pages 44–45, 608, 618). Deighton discusses Lamb wave dispersion in Abstract 7.4, UI85 Conference, London, July 2–4, 1985 in the Supplement to ULTRA3 23 (4), 1985.

Figure 1:
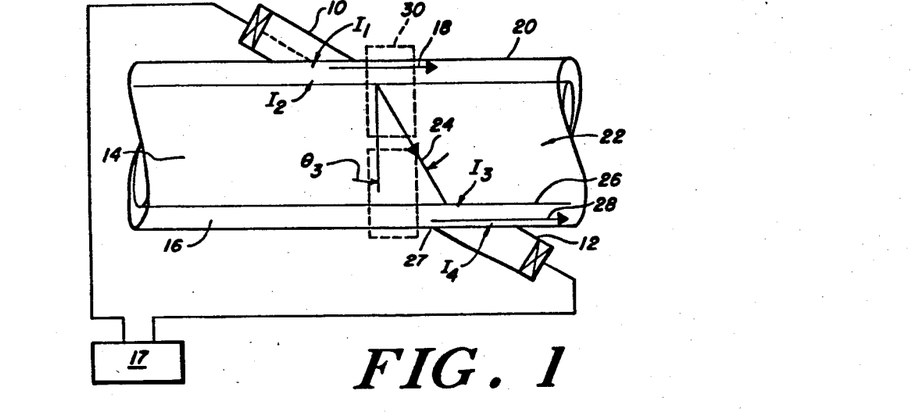
FIG. 1 is a schematic representation of a general arrangement for practicing the invention.

Referring now to FIG. 1, in a representative embodiment in accordance with the invention, a first transducer 10 and a second transducer 12 are positioned along a conduit 14 having a flow of a fluid, for example water, passing therethrough. The transducers 10 and 12 can be of the clamp-on type and can be held to the conduit wall 16 by, for example, magnetic or mechanical forces. In accordance with the invention, the transducer 10 has a construction which responds to the excitation pulse signal from an ultrasonic flowmeter operating system 17, as is well known in the art, to launch a Rayleigh-like surface wave illustrated at 18 along the wall surface 20 of the conduit. The excitation pulse is a short spike-like signal of limited duration, as discussed above.

For purposes of the discussion which follows hereinafter, that surface 20 of the wall (or other plate-like structure) on which a transducer is in contact for transmitting or receiving a surface wave is designated a local surface to the transducer and that surface of the wall (or other plate-like structure) from which a Rayleigh-like surface wave "leaks" into or out of a fluid is hereinafter called the "remote" surface. Thus, in accordance with the invention, transducer 10 launches a surface wave on the local surface 20 of conduit wall 16. The surface wave is, as noted above, a Rayleigh-like surface wave and attenuates significantly the farther from the local surface it penetrates into the solid. The illustrated Rayleigh-like surface wave propagates along the surface of the solid in an axial direction away from transducer 10.

Applicant has recognized that a portion of the energy in the Rayleigh-like surface wave launched by transducer 10 will leak into a fluid 22 flowing through conduit 14. At the fluid/wall interface, a wave having a substantially attenuated intensity is "launched" and is represented by, for example, wave 24. Wave 24 traverses the fluid, at an oblique angle to the axis of the conduit. The refracted angle, $\theta_3$, of the wave 24 can be determined according to Snell's law. When the liquid-borne wave reaches the opposite wall, at remote surface 26 of transducer 10, a new wave is launched in the pipe wall and a yet substantially further diminished Rayleigh-like surface wave at local surface 27 will be generated by the waves within the opposite pipe wall as illustrated at 28. This surface wave, even though its intensity may be greatly diminished compared to the initial intensity at transducer 10, still has enough coherent energy to produce a desired signal intensity and thereby provide a received signal at transducer 12 to be detected above the background noise. The principal reason for the adequacy of signal strength is that numerous parallel rays arrive simultaneously at the receiving transducer. The received signal can be processed by the operating system 17, as is well known in the art, for determining for example a transit time in the fluid. The FIG. 1 configuration can thus be adapted as for example a transit time flowmeter.

FIG. 1 also illustrates a damping apparatus 30 which can be placed selectively around the pipe and held in place by clamping or otherwise. If the acoustic wave impedance of the dampener and the interfering surface wave type (that is, the circumferentially-spreading Rayleigh-like surface wave) are approximately matched, a short circuit can be efficiently coupled into the dampener whereby the energy of the wave is absorbed. In this way the Rayleigh-like waves may be confined to only useful regions of the plate or pipe.

Figure 2:
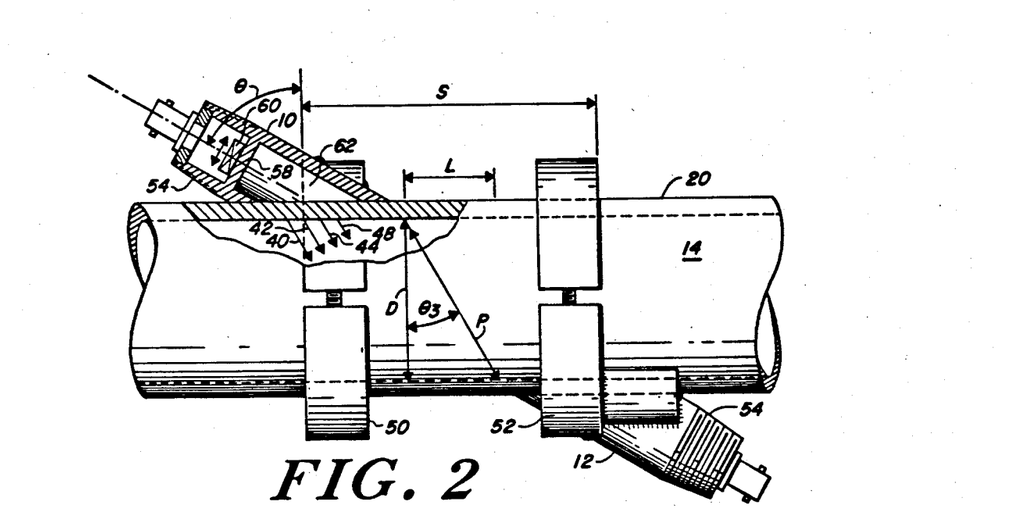
FIG. 2 shows a Rayleigh-like surface wave transit time flowmeter having transducers clamped mechanically to a pipe in accordance with the invention.

Referring to FIG. 2, which illustrates in greater detail one form of transducer which can be coupled to the pipe or conduit, in one particular embodiment of the invention, the transducers 10 and 12 can be wedge transducers similar to those that can be used to launch and detect shear waves as illustrated in Lynnworth, *Trans. Inst. MC*, Vol. 4, No. 1, p. 6 (January-March, 1982). The coherent elements of energy flux radiated diagonally across the pipe, are represented by oblique waves such as waves 40, 42, 44, 48. The transducers 10 and 12 of FIG. 2 are clamped tightly to the pipe using encircling collars 50, 52 respectively, similar to those shown in Lynnworth, U.S. Pat. No. 4,286,470.

Figures 9, 10:
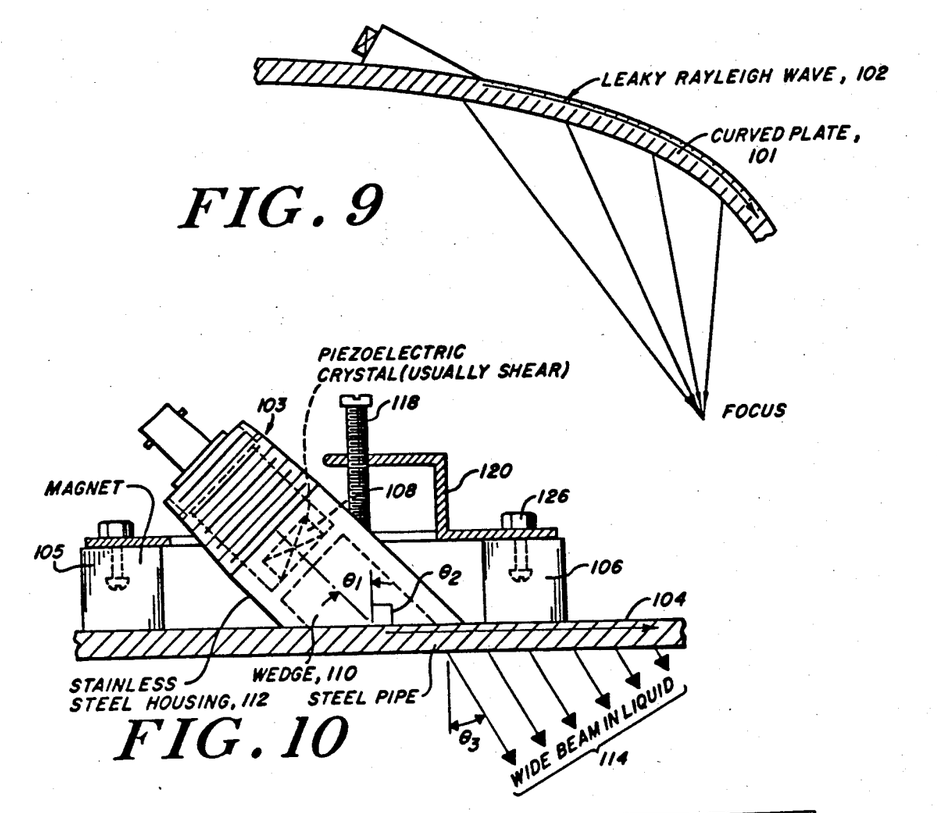
FIG. 9 shows a plate having a curvature for focusing a fluid wave at a selected position.
FIG. 10 shows a magnetically coupled transducer assembly according to the invention.

In addition, it is also possible to use magnetic clamps to hold the transducers in place on magnetic pipes composed, for example, of iron or steel, at least for short durations as in feasibility studies or in flow studies. One such arrangement, illustrated in FIG. 10, is similar in design to the transducer arrangement of Lynnworth et al, U.S. Pat. No. 4,320,659, at FIG. 6. Since the transducers are often applied on the sides of a horizontal pipe, the weight of the transducer must then be less than the holding force of the magnet, less the coupling force, and less other forces such as, for example, the pull of the cable which is connected to the transducer.

Referring again to FIG. 2, the conduit 14 is, as noted above, encircled by two-piece collars 50 and 52. The collars can also be, for example, those commercially available as standard components from manufacturers such as Ruland and Stafford. Housings 54 which hold the transducers are generally cylindrical housings formed, for example, of three-quarter inch pipe nipples, threaded at one end to accommodate a junction box or conduit connecting union, and chamfered at the other end to provide the correct angle of incidence, typically between 30° and 60°, as required for launching or detecting Rayleigh-like surface waves. The pipe nipple 24 can be divided into two cavities by a plate 58 which either is thin compared to the wavelength of excitation, or can be a multiple of half wavelengths. The wedge is then installed in the chamfered cavity. A crystal 60, usually, but not necessarily of the vertically polarized shear mode type, is bonded to one side of the plate 58. Alternatively, the crystal can be bonded directly to the wedge 62 in the absence of such a plate. The diameter or width of the crystal 60 is preferably in the range from approximately one to ten Rayleigh wavelengths ($\lambda_R$ to $10\lambda_R$).

The wedge can be sealed in the cavity by a thin shim of stainless steel, typically fifty micrometers thick (0.002 inches). The assembly is coupled by a silicon rubber, epoxy, grease, or other substance, to the outer surface 20 of the conduit, the local surface, so that Rayleigh-like surface waves can be launched or detected along an extended surface of the conduit. The Rayleigh waves thus convert and leak diagonally across the fluid in the pipe as represented by the rays 40, 42, 44, 48.

The refracted angle of the waves, $\theta_3$, determines the diagonal path length in the fluid. That diagonal path length is designated as "P" and the inside diameter of the pipe is denoted by "D". The axial spacing S between the two transducers is defined by the intersection of the oblique centerlines of each of the transducer assemblies with the pipe exterior. For ease of use, these intersections preferably are made to coincide, with a commercial instrument, with the outboard sides of the collars 50 and 52 as in the illustrated embodiment. In practice, however, deviations from this idealized picture occur because of beam spread in the wedge, variability of the sound speed $c_1$ in the wedge, mechanical tolerances in clamp manufacture, etc.

Figure 3:
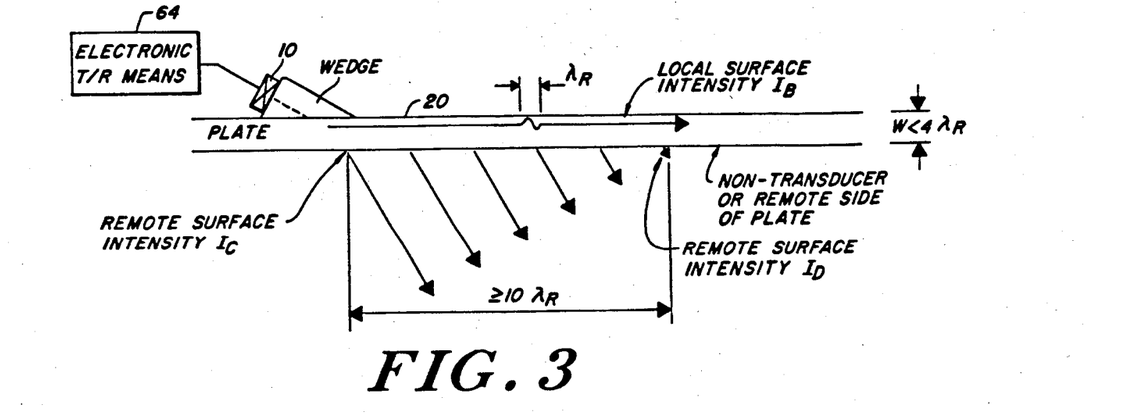
FIG. 3 is a diagrammatic representation illustrating the practical considerations limiting the invention.

In accordance with the present invention, and referring now to FIG. 3, if the wavelength of the wave, as a Rayleigh-like surface wave is designated as $\lambda_R$, then the maximum wall or plate thickness w, according to the invention, must be less than approximately four wavelengths ($4\lambda_R$). In addition, it has been shown that attenuation of a surface wave on an elastic "half-space" due to radiation back into an adjacent liquid in some cases amounts to a factor of 1/e over a path of approximately ten wavelengths. Generally, the greater the density difference between the plate and the remote fluid, the less will be the excess attenuation per wavelength due to leakage into the remote fluid. Thus, as shown in FIG. 3, the "extended aperture" is defined herein to be a distance, measured in the direction of Rayleigh wave propagation, of at least ten Rayleigh wavelengths ($10\lambda_R$). Thus, for a transducer 10 coupled to the local surface 20 and excited by pulse source 64, one would expect a synthetic aperture which extends, in the axial direction, at least ten Rayleigh wavelengths. In addition, the thickness of the structure across which an attenuated Rayleigh wave is to be "leaked" into the adjacent fluid, at the remote surface of the structure, shall be less than approximately four wavelengths and preferably not less than approximately one-half wavelength.

In accordance with this illustrated embodiment of the invention, referring to FIG. 2, the axial interaction length in the fluid, L, is given by $L = D \tan \theta_3$. In a transit time ultrasonic flowmeter, the flow velocity measured along a path such as P can be measured from the equation $V = c_3^2 \, dt/2L$ where dt is the time difference between the upstream and downstream transit times. In the illustrated embodiment, it is important to note that the spacing S is not critical, provided it is a known quantity. The wall thickness should also be known, first so that one does not waste time attempting a measurement with the wrong frequency (although the present method and apparatus is significantly more tolerant of uncertainties in wall thickness than other methods), but second so that the time delay through the wall thickness can be properly taken into account. Also, to compute volumetric flow rates, the pipe area must be known.

In a typical example, consider a steel pipe filled with water and surrounded by air near room temperature. Leakage of the Rayleigh wave into the air occurs at or near the refracted angle $\theta_{1R} = \sin^{-1}(343/3000)$ or 6.6° on the local side. Leakage into the water occurs at a refracted angle $\theta_3$ of 30°. In a particular embodiment of the invention, considering the flow of water in steel pipe, if the speed of sound in the water is taken as $c_3 = 1,500$ meters per second, and if the Rayleigh velocity in the steel pipe is approximated as $c_R = 3,000$ meters per second, and if the speed of sound of the incident wave in the wedge transducer 12 is 2,121 meters per second, then at an incident angle of about 45°, the Rayleigh wave will be launched into the pipe. The leakage of mode converted longitudinal waves in the water will occur at a refracted angle of 30° ($\theta_3$). For comparison purposes, shear waves, having a speed in the pipe of 3,230 meters per second, and incident at the steel/water interface at an angle of 60°, would refract at an angle of only 23.7° into the water. Further, achieving a refracted angle of 30° is especially important where interrogation over a midradius chord is required in order to minimize the influence of flow profile uncertainties on the meter factor.

Other methods for launching Rayleigh waves and detecting the surface waves can be employed. Thus, for example, periodic arrays, which can be designed to add less mass to the substrate than a wedge would add, can, for some applications, provide an advantage over the wedge. And, as is well known, interdigital methods are in common use for high frequency surface wave applications above approximately ten megahertz. Even absorption of laser energy can be adapted to launch Rayleigh waves.

Figure 4:
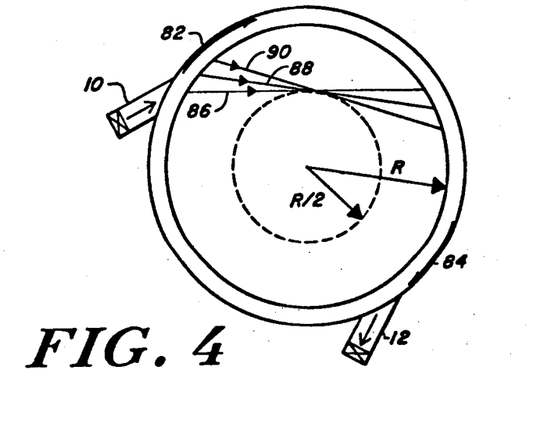
FIG. 4 is an end view of a pipe showing the circumferential Rayleigh generated wave along a midradius chord according to the invention.

In contrast to the axially extended source and detection regions of FIGS. 1, 2 and 3, and referring to FIG. 4, the transducers 10 and 12 can be oriented for providing a circumferentially directed extended region as is advantageous in some forms of ultrasonic correlation flowmeters. Transducer assemblies 10 and 12, in accordance with this aspect of the invention, transmit and receive respectively, Rayleigh-like surface waves designated 82 and 84, respectively. In a correlation flowmeter, the contribution due to chordal paths 86, 88 and 90, are important in forming the received and detected Rayleigh-like surface wave 84. Using Snell's law, it can be shown that for water in a steel pipe, under ordinary conditions, the chordal paths may be the midradius chordal paths which are particularly advantageous as noted in Lynnworth, U.S. Pat. No. 4,103,551. The midradius chordal paths have a preferred profile weighting property (and a meter factor substantially unity) for laminar and turbulent flow. For clamp-on applications in a round pipe, midradius chordal interrogation requires a refracted angle of 30° as measured from an end view of the pipe.

Figure 5:
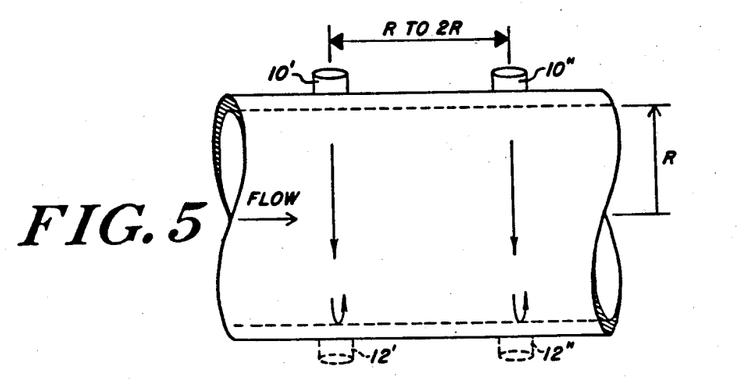
FIG. 5 is a side elevation view corresponding to FIG. 4 using two pairs of circumferentially directed Rayleigh transducers.
Figure 6:
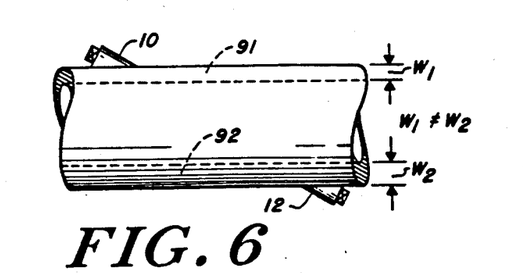
FIGS. 6–8 illustrate various clamp-on configurations in which the wall has a varying thickness according to the invention.

In another particular embodiment of a correlation type flowmeter according to the invention, referring to FIG. 5, two pairs of transducers 10', 12' and 10'', 12'' are axially separated, as illustrated in FIG. 5, by a distance between one and four times the radius of the pipe. The transmitting transducers launch Rayleigh-like surface waves as illustrated in FIG. 4. Measurements can be made by through transmission, or by pulse echo techniques. In correlation measurements of the type that is described here, suppression of the acoustic short circuit pipe wall noise can be accomplished by the aforementioned dampening method or by the quadrature techniques such as those described by Jacobson et al in *Ultrasonics*, May 1985.

Figure 7:
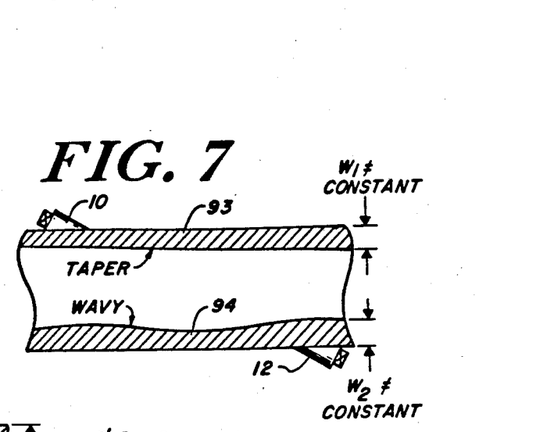
Figure 8:
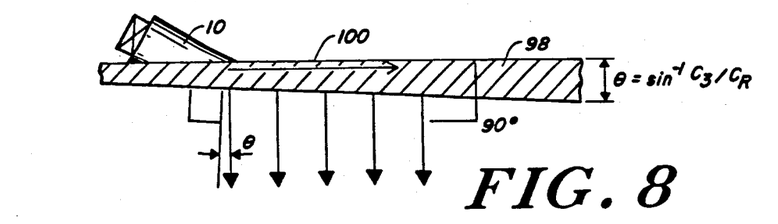

Referring now to FIGS. 6–9, the clamp-on method and apparatus of FIGS. 1–3 can be advantageously employed in connection with conduits (or other plate-like structures) in which the opposite walls 91, 92 are of unequal thickness (FIG. 6) or wherein the walls are either tapered (wall 93) or of uneven thickness (wall 94) (FIG. 7). In addition, referring to FIG. 8, a plate or wall 98 can be intentionally tapered to provide a radiation direction in the fluid which is orthogonal to the local surface 100. In accordance with this embodiment of the invention, illustrated in FIG. 8, the angle of taper is equal to the angle of refraction of the wave, which then causes the wave launched in the fluid to be in a direction which is orthogonal to the local surface.

In a similar manner, referring to FIG. 9, the wall can be curved so that the resulting refracted wave in the fluid is focused onto a selected position within, for example, the fluid domain. In accordance with this embodiment of the invention, the curvature of the wall 102 varies along the arc to provide the correct "direction" to the leaking Rayleigh-like surface wave 102.

Referring now to FIG. 10, a transducer assembly 103 is coupled against a pipe wall 104 with the coupling force being supplied by a pair of small magnets 105, 106 straddling the transducer. The transducer includes a piezoelectric crystal 108 which is arranged to provide a shear wave output to a wedge element 110. The wedge and crystal structure is housed in a stainless steel housing 112. The output of this configuration is, as illustrated in FIG. 2, a wide beam wave 14 refracted at an angle $\theta_3$. In other embodiments of the invention, a somewhat stronger horseshoe magnet can be used to hold the transducer in place against the pipe wall 102. In either magnet configuration, cantilevered clamp 120, for example, can be employed for securing the transducer assembly to the conduit. In the illustrated embodiment, a screw element 118, supported by clamp 120 holds transducer assembly 103 in place. Clamp 120 is secured to the magnet assembly by a screw element 126. The screw 118 is normally tightened only finger tight against the housing 112.

Figure 11:
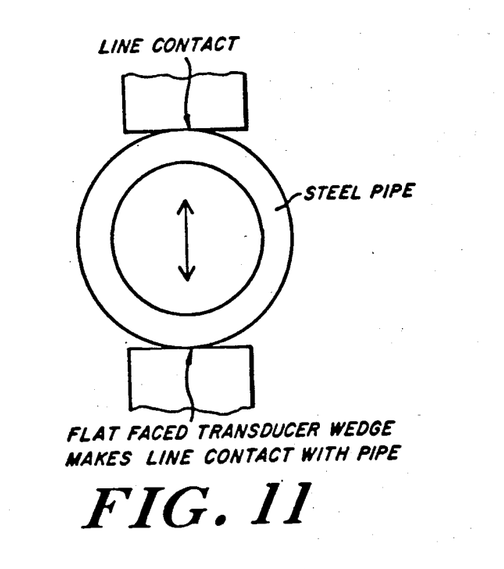
FIG. 11 is an end view showing the line of contact of flat face transducers according to the invention.

Referring now to FIG. 11, which is an end view showing transducer assembly to conduit contact of the structure illustrated in FIG. 10, the wedge elements make a line contact with the circular conduit. Despite the resulting immediate beam spread, the line contact is usually adequate since the couplant usually spreads the actual contact area somewhat. The line contact enables a single pair of flat faced wedges to be coupled to pipes or curved vessels having a wide range of curvatures or diameters. The relaxed condition that the thickness of the wall only need be less than four Rayleigh wavelengths, enables the same pair of transducers to be used over a wide range of wall thicknesses. The received waveform, which can be broadband, varies somewhat with wall thickness.

Figure 12:
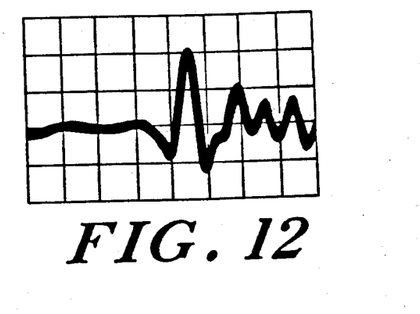
FIG. 12 is an example of a broadband 500 kilohertz received signal obtained using a four-inch Schedule 40 steel pipe filled with water in accordance with the invention.

Referring to FIG. 12, in one example, a received 500 kilohertz broadband signal obtained using a 4" steel pipe, water-filled, and with one traverse, is illustrated. The excitation source is a pulsed signal to the transmitting transducer. The broad electrical bandwidth is indicated by the rapid rise, within one cycle, to full maximum amplitude. This is very different from the narrowband waveforms obtained using, for example, dispersive Lamb waves, which necessarily take several cycles to reach full amplitude (maturity). The one particular pair of transducers used to generate this illustrative waveform has been successfully used on steel pipes having nominal diameters of 2, 4, 8, 16, and 186 inches.

Figure 13:
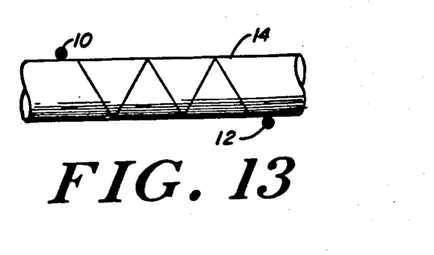
FIG. 13 shows a particular embodiment having a zigzag interrogation path in accordance with the invention.

Referring now to FIG. 13, the Rayleigh-like surface wave generating structure can also be employed in a zigzag clamp-on interrogation configuration to improve the resolution of the data in proportion to the number of traverses. Thus, a five-fold increase is available for the configuration illustrated in FIG. 13 (for a small diameter pipe).

Figure 14:
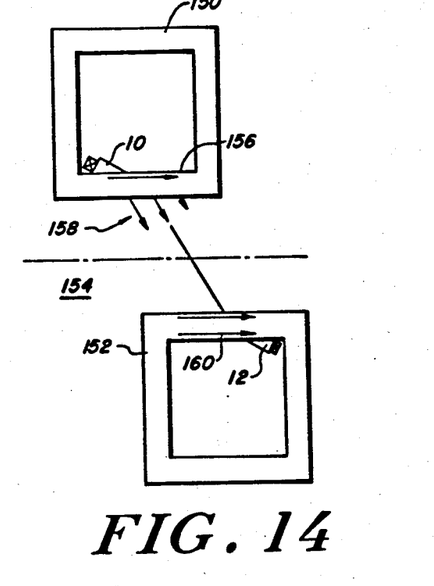
FIG. 14 shows a "wetted" transducer assembly according to a particular embodiment of the invention.

In another aspect of the invention, referring to FIG. 14, the surface wave generating transducers 10, 12 can be contained and fully enclosed in box structures 150, 152, respectively. These are so-called wetted transducers where each transducer is within an immersed sealed compartment, the box structure 150, 152, and the fluid 154 flows therebetween. In operation, the structure is functionally identical to that of, for example, FIG. 3. In particular, the box structure 150 has a transducer assembly 10 mounted therein in contact with a "local" surface 156 whereby the transducer operates to launch a Rayleigh-like surface wave on the interior local surface of the structure 150. The resulting Rayleigh-like surface wave 158 generates a leakage wave which traverses the fluid 154 in which the wetted transducers are immersed. The second box structure 152 enables detection of the signal energy arriving thereat. The second box structure contains the receiving transducer assembly 12 which detects the received Rayleigh-like surface wave 160 and thereby enables recognition of the fluid characteristic being interrogated, such as volumetric or mass flow.

Figure 15:
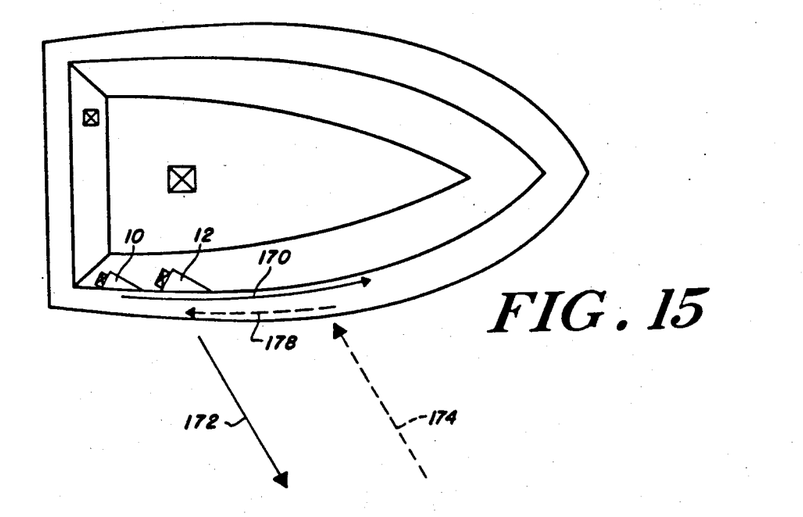
FIG. 15 shows a transducer assembly in a floating vessel according to the invention.

In another aspect of the invention, referring to FIG. 15, the transducer assemblies 10, 12 can be mounted within a floating vessel having, for example, an aluminum shell. The resulting generated Rayleigh-like surface waves 170 from transmitting transducer 10 provide an outwardly directed interrogation signal 172 which can be employed for detecting objects within the water. Reflected signals 174 from objects in the water cause received Rayleigh-like surface wave 178 to be created, and received and detected by receiving transducer 12.

In another application of the invention, using either pulse echo or transmission techniques, the coupling of energy from the remote surface into an adjacent liquid can be interpreted in terms of a liquid level measurement.

Additions, subtractions, deletions, and other modification of the disclosed particular embodiments of the invention will be apparent to those practiced in the art and are within the scope of the following claims.

What is claimed is:

1. Apparatus for measuring a characteristic of a fluid comprising
   a solid plate-like material having a local surface and a remote surface, said remote surface being in contact with the fluid,
   a transducer means,
   means for coupling said transducer means to said local surface of said solid material,
   means for exciting said transducer means for generating along said local surface, Rayleigh-like surface waves having a wavelength $\lambda_R$ in said solid material,
   said local surface and said remote surface having a separation, in an interrogation direction, less than four wavelengths ($4\lambda_R$), and
   said interrogation direction extending normal to said local surface.

2. The measuring apparatus of claim 1 wherein
   said solid plate-like material forms a wall of a conduit and said characteristic being measured is fluid flow within the conduit.

3. The apparatus of claim 2 wherein said conduit has a conduit wall of varying thickness.

4. The apparatus of claim 2 wherein
   said conduit has a first conduit wall having a thickness which is different from the thickness of a second conduit wall.

5. The apparatus of claim 2 wherein said coupling means comprises
   means for coupling said transducer for generating said Rayleigh-like surface waves in an axial direction along said conduit, and
   further comprising
   a second transducer means, and
   means for coupling said second transducer means to said conduit for receiving Rayleigh-like surface waves.

6. The apparatus of claim 2 wherein said coupling means comprises
   means for coupling said transducer to said conduit for launching Rayleigh-like surface waves in a circumferential direction relative to said conduit.

7. The apparatus of claim 6 wherein said coupling means comprises
   means for coupling said transducer at an angle for generating interrogation waves within said conduit along midradius chords of said conduit.

8. The apparatus of claim 2 further wherein said coupling means comprises
   means for coupling said transducer to said local surface for generating a synthetic aperture along said remote surface of said conduit wall having an extent of at least ten wavelengths ($10\lambda_R$).

9. The apparatus of claim 1 wherein said plate-like solid material comprises
   a curved plate-like material having a varying curvature for focusing fluid-borne interrogation signals, generated from said Rayleigh-like surface waves, at a position in said fluid.

10. The apparatus of claim 1 wherein said transducer means has a width between about one and ten wavelengths ($\lambda_R$–$10\lambda_R$).

11. Apparatus for measuring a characteristic of a fluid comprising
   a solid plate-like material having a local surface and a remote surface, said remote surface being in contact with the fluid,
   a transducer means,
   means for coupling said transducer means to said local surface of said solid material,
   means for exciting said transducer means for generating along said local surface, Rayleigh-like surface waves having a wavelength $\lambda_R$ in said solid material,
   said local surface and said remote surface having a separation, in an interrogation direction, greater than one-half of a wavelength ($\lambda_R/2$),
   said interrogation direction extending normal to said local surface, and
   said Rayleigh-like surface waves
      are non-dispersive, and
      have an intensity at said remote surface substantially less than the intensity at the local surface.

12. The measuring apparatus of claim 11 wherein said solid plate-like material forms a wall of a conduit and said characteristic being measured is fluid flow within the conduit.

13. The apparatus of claim 12 wherein said conduit has a conduit wall of varying thickness.

14. The apparatus of claim 12 wherein
   said conduit has a first conduit wall having a thickness which is different than the thickness of a second conduit wall.

15. The apparatus of claim 12 wherein said coupling means comprises
   means for coupling said transducer for generating said Rayleigh-like surface waves in an axial direction along said conduit, and
   further comprising
   a second transducer means, and
   means for coupling said second transducer means to said conduit for receiving Rayleigh-like surface waves.

16. The apparatus of claim 12 wherein said coupling means comprises
   means for coupling said transducer to said conduit for launching Rayleigh-like surface waves in a circumferential direction relative to said conduit.

17. The apparatus of claim 16 wherein said coupling means comprises
   means for coupling said transducer at an angle for generating interrogation waves within said conduit along midradius chords of said conduit.

18. The apparatus of claim 11 wherein said plate-like solid material comprises
   a curved plate-like material having a varying curvature for focusing fluid-borne interrogation signals, generated from said Rayleigh-like surface waves, at a position in said fluid.

19. The apparatus of claim 11 wherein said exciting means includes
   means for generating a pulse excitation signal for said transducer means having a pulse duration less than the wall thickness of said plate-like material divided by the velocity of the waves in the solid material.

20. Apparatus for measuring a characteristic of a fluid comprising
   a solid plate-like material having a local surface and a remote surface, said remote surface being in contact with the fluid,
   a transducer means,
   means for coupling said transducer means to said local surface of said solid material,
   means for exciting said transducer means with a pulse signal sufficiently short to prevent intra-wall interference of said energy for generating along said local surface, Rayleigh-like surface waves having a wavelength $\lambda_R$ in said solid material,
   said local surface and said remote surface having a separation, in an interrogation direction, less than four wavelengths ($4\lambda_R$),
   said interrogation direction extending normal to said local surface, and
   said Rayleigh-like surface waves
      are non-dispersive, and
      have an intensity at said remote surface substantially less than the intensity at the local surface.

21. The apparatus of claim 20 wherein said exciting means includes
   means for generating a pulse excitation signal for said transducer means having a pulse duration less than the wall thickness of said plate-like material divided by the velocity of the waves in the solid material.

22. A clamp-on ultrasonic flowmeter for measuring a characteristic of a fluid flowing in a conduit formed with a solid material wall having a local surface and a remote surface comprising
   a first and a second transducer means,
   means for coupling said first and second transducer means to said local surface of said conduit wall in an axially spaced relationship along said local surface of said conduit wall,
   means for selectively exciting said transducer means for generating, along said local surface of said conduit wall relative to said excited transducer means, Rayleigh-like surface waves having a wavelength $\lambda_R$ in said conduit wall,
   said conduit having a wall thickness less than four wavelengths ($4\lambda_R$), said wall thickness being measured in a direction normal to propagation of said surface waves along said conduit.

23. A clamp-on ultrasonic flowmeter for measuring a characteristic of fluid flowing in a conduit having a local surface and a remote surface comprising
   a first and a second transducer means,
   means for coupling said first and second transducer means to said local surface of said conduit in an axially spaced relationship along said outside local surface of said conduit,
   means for selectively exciting said first and second transducer means for generating along said local surface Rayleigh-like surface waves having a wavelength $\lambda_R$ in said conduit,
   said conduit having a wall thickness greater than one-half of a Rayleight wavelength ($\lambda_R/2$), and
   said Rayleigh-like surface waves
      being non-dispersive, and
      having an intensity at a conduit-fluid interface substantially less than the intensity at the local surface.

24. A clamp-on ultasonic flowmeter for measuring a characteristic of a fluid flowing in a conduit having a local surface and a remote surface comprising
   a first and a second transducer means, means for coupling said first and second transducer means to said local surface of said conduit in an axially spaced apart relationship along said local surface of the conduit, means for selectively exciting said first and second transducer means with a pulse signal sufficiently short to prevent intra-wall interference of said energy for generating along said local surface Rayleigh-like surface waves having a wavelength $\lambda_R$ in said conduit to produce fluid characateristic measuring waves at a conduit fluid interface.

25. A method for measuring a characteristic of a fluid comprising contacting a remote surface of a plate-like solid material with said fluid, coupling a transducer to a local surface of a solid material for transmitting Rayleigh-like surface waves in said material, exciting said transducer for generating said Rayleigh-like surface waves having a wavelength in said material of $\lambda_R$, and selecting a frequency of excitation for said transducer whereby a wall thickness between the local surface and a remote surface of said solid plate-like material is less than four Rayleigh wavelengths ($4\lambda_R$).

26. The method of claim 25 wherein said solid material is formed as a wall of a conduit, said coupling step comprises the step of coupling said transducer for generating said Rayleigh-like surface waves in an axial direction along said conduit, and further comprising the step of coupling a second transducer means to said conduit for receiving Rayleigh-like surface waves.

27. The method of claim 28 further wherein said coupling step comprises the step of coupling said transducer to said local surface for generating a synthetic aperture along said remote surface of said conduit wall having a extend of at least ten wavelengths ($10\lambda_R$).

28. The method of claim 25 wherein said material is formed as wall of a cylindrical conduit and said coupling step comprises the step of coupling said transducer to said conduit for launching Rayleigh-like surface waves in a circumferential direction relative to said conduit.

29. The method of claim 28 wherein said coupling step comprises the step of coupling said transducer at an angle for generating interrogation waves within said conduit along mi-dradius chords of said conduit.

30. A method for measuring a characteristic of a fluid comprising the steps of contacting a remote surface of a plate-like solid material with said fluid, coupling transducer to a local surface of said plate-like solid material for transmitting Rayleigh-like surface waves along said local surface, and exciting said transducer means with pulse signals sufficiently short to prevent intra-wall interference of said energy, to produce fluid characteristic interrogation waves at an interface between said plate-like sold material and said fluid.

31. The method of claim 30 wherein said place like solid material is formed as the wall of a conduit and said coupling step comprises the steps of coupling said transducer for generating said Rayleigh-like surface waves in an axial direction along said conduit, and further comprising the step of coupling a second transducer means to said conduit for receiving a Rayleigh-like surface waves.

32. The method of claim 31 further wherein said coupling step comprises the step of coupling said transducer to said local surface for generating a synthetic aperture along said remote surface of said conduit wall having a extent of at least ten wavelengths ($10\lambda_R$).

33. The method of claim 30 wherein said plate like solid material is formed as the wall of a conduit and said coupling step comprises the step of coupling said transducer to said conduit for launching Rayleigh-like surface waves in a circumferential direction relative to said conduit.

34. The method of claim 33 wherein said coupling step comprises the step of coupling said transducer at an angle for generating interrogation waves within said conduit along mi-dradius chords of said conduit.

35. A method for measuring a characteristic of a fluid comprising the steps of contacting a remote surface of a solid plate-like material with the fluid, coupling a transducer means to a local surface of said plate-like solid material, exciting said transducer means for generating along said local surface, Rayleigh-like surface waves having a wavelength $\lambda_R$ in said solid plate-like material, and said Rayleigh-like surface waves
are non-dispersive, and
have an intensity at said remote surface of said solid material, substantially less than the intensity at the local surface.

36. The method of claim 35 wherein said plate like solid material is formed as the wall of a conduit, said coupling step comprises the step of coupling said transducer for generating said Rayleigh-like surface waves in an axial direction along the wall of said conduit, and further comprising the step of coupling a second transducer means to said conduit for receiving Rayleigh-like surface waves.

37. The method of claim 36 further wherein said coupling step comprises the step of coupling said transducer to said local surface for generating a synthetic aperture along said remote surface of said conduit wall having a extent of at least ten wavelengths ($10\lambda_R$).

38. The method of claim 35 wherein said plate like solid material is formed as the wall of a conduit and said coupling step comprises the step of coupling said transducer to said conduit for launching Rayleigh-like surface waves in a circumferential direction relative to said conduit.

39. The method of claim 38 wherein said coupling step comprises the step of coupling said transducer at an angle for generating interrogation waves within said conduit along mi-dradius chords of said conduit.

40. A method for measuring a characteristic of a fluid comprising the steps of contacting a remote surface of a solid plate-like material with the fluid, coupling a transducer means to a local surface of a said solid material, exciting said transducer means with a pulse signal sufficiently short to prevent intra-wall interference of said energy for generating along said local surface, a Rayleigh-like surface wave, having a wavelength $\lambda_R$ in said solid plate-like material, selecting a frequency of excitation for said transducer whereby said local surface and said remote surface have a separation, in an interrogation direction, greater than one half of a wavelength ($\lambda_R/2$) and less than four wavelengths ($4\lambda_R$), said interrogation direction extending normal to said local surface, and said Rayleigh-like surface wave
is non-dispersive, and
has an intensity at said remote surface of said solid material, substantially less than the intensity at the local surface.

* * * * *

UNITED STATES PATENT AND TRADEMARK OFFICE
CERTIFICATE OF CORRECTION

PATENT NO. : 4,735,097
DATED : April 5, 1988
INVENTOR(S) : Lawrence C. Lynnworth It is certified that error appears in the above-identified patent and that said Letters Patent is hereby corrected as shown below:

<u>In the Drawings</u>:

In Figure 5 on Sheet 2 change "R to 2R" to --R to 4R--, as shown in the attached corrected Figure 5.

Signed and Sealed this

Third Day of October, 1989

*Attest:*

DONALD J. QUIGG

*Attesting Officer*  Commissioner of Patents and Trademarks

FIG. 5